(12) United States Patent
Anderson

(10) Patent No.: US 6,694,980 B2
(45) Date of Patent: Feb. 24, 2004

(54) PROPHYLACTIC GARMENT SYSTEM FOR SAFER SEX

(75) Inventor: Amy Lee Anderson, Richmond, CA (US)

(73) Assignee: Amy L. Anderson, Pinole, CA (US)

( * ) Notice: Subject to any disclaimer, the term of this patent is extended or adjusted under 35 U.S.C. 154(b) by 49 days.

(21) Appl. No.: 10/074,505

(22) Filed: Feb. 11, 2002

(65) Prior Publication Data
US 2003/0150463 A1 Aug. 14, 2003

(51) Int. Cl.⁷ .................................................. A61F 6/02
(52) U.S. Cl. ........................ 128/842; 128/844; 128/918; 206/69
(58) Field of Search ............................... 128/842, 844, 128/918; 604/347–353; 206/69

(56) References Cited

U.S. PATENT DOCUMENTS

| | | |
|---|---|---|
| 4,637,078 A | 1/1987 | Southwell |
| 4,660,551 A | 4/1987 | Nishimura |
| 4,664,104 A | 5/1987 | Jaicks |
| 4,781,709 A | 11/1988 | Grubman |
| 4,807,611 A | 2/1989 | Johnson |
| 4,834,113 A | 5/1989 | Reddy |
| 4,834,114 A | 5/1989 | Boarman |
| 4,840,624 A | 6/1989 | Lee |
| 4,862,901 A | 9/1989 | Green |
| 4,942,885 A | 7/1990 | Davis et al. |
| 5,172,430 A * | 12/1992 | Lerma-Solis .................. 206/61 |
| 5,181,527 A | 1/1993 | Dorsey et al. |
| 5,269,320 A | 12/1993 | Hunnicutt |
| 5,283,912 A | 2/1994 | Chung |
| 5,299,434 A | 4/1994 | Kaufman |
| 5,460,188 A | 10/1995 | Barrett, Sr. |
| 5,535,757 A | 7/1996 | Fleming, Jr. |
| 5,687,741 A | 11/1997 | Torger |
| 5,794,769 A | 8/1998 | Tomlinson et al. |
| D399,987 S | 10/1998 | Bradley |
| 5,984,910 A | 11/1999 | Berke |

* cited by examiner

Primary Examiner—Michael A. Brown
(74) Attorney, Agent, or Firm—Morrison & Foerster LLP

(57) ABSTRACT

A prophylactic system or kit that prevents the transmission of disease-producing microorganisms and spermatozoa by acting as a sexual barrier and sexual aid. The invention comprises an undergarment that allows sex acts while the garment is worn and that absorbs the fluids associated with the sex act, at least one pocket, sexual aids, and safer-sex information.

9 Claims, 4 Drawing Sheets

PROPHYLACTIC GARMENT SYSTEM FOR SAFER SEX

FIELD OF THE INVENTION

This invention relates to a prophylactic system which acts as a sexual barrier for preventing the transmission of disease-producing microorganisms and spermatozoa.

Specifically, the invention relates to an undergarment which can accommodate penetration while readily providing various sexual aids, and safer-sex information.

BACKGROUND OF THE INVENTION

Because the number of people who have been infected with sexually transmitted diseases, or STDs, has grown rapidly over the last decades, the need for safer-sex aids has reached critical levels. Female and male condoms are not always available during the moments prior to the initiation of sex acts, and when available, are not always used properly. Many are unaware of the proper use of or do not have proper access to condoms and sexual aids, such a lubricants. Condoms, although effective if properly used, can only cover the penis and do not provide protection for the areas surrounding the genitalia, nor can they prevent the intermingling of body fluids. Therefore what is needed, is a safer-sex device which is highly effective in preventing disease transmission by educating sexual partners, limiting the exchange of body fluids and disease producing microorganisms, and providing the appropriate sexual aids to assist in a reduction in disease-transmission.

Male condoms are known and have been available for centuries. Female condoms, although introduced relatively recently, are also commonly known. Undergarments that incorporate prophylactics for the purpose of preventing pregnancy and sexually transmitted disease have been proposed in prior patents, however, no other previous designs teach the optimal combination of features that are taught by the present invention. U.S. Pat. No. 4,664,104 by Jaicks describes an anti-herpes modality system in which a removable condom is attached to a panty made of non-breathable material. U.S. Pat. No. 4,834,114 by Borman shows a contraceptive system having a one-piece formation to be worn by males and females. It includes an integral triangular-shaped shield, to each end of which shield straps are attached. The straps are tied around the person's torso to hold the shield in place. U.S. Pat. No. 4,637,078 by Southwell teaches a panty-styled undergarment designed for the handicapped which includes a removable panel which exposes the vagina. It was not designed with the idea of having intercourse and provides no contraceptive protection. U.S. Pat. No. 4,862,901 by Green, U.S. Pat. No. 5,269,320 by Hunnicutt, and U.S. Pat. No. 5,181,527 by Dorsey each describe a panty in which a liquid impervious panel is integral to the lower portion of the panty. The panel includes a collapsed tubular portion which is supposed to expand a collapsed tubular portion which is supposed to expand outward when a penis enters the vaginal area. U.S. Pat. No. 4,834,113 by Ready proposes a rolled, rather than a telescoped, portion forming an integral condom attached to a non-breathable undergarment. U.S. Pat. No. 5,687,741 discloses a woman's panty-type undergarment that provides a means of attaching a releasable, securable, and disposable female condom that can be comfortably worn for hours before anticipated intercourse. The device uses a resilient, ovoid condom attachment member that is sewn or otherwise attached to an opening in the crotch portion of the panty. U.S. Pat. No. 5,535,757 discloses a combination of a bottom undergarment and a prophylactic that has an opening in the crotch of the undergarment and a base. The base includes snaps which allow the base to be snapped into a receptacle on the undergarment after a condom is affixed to the base.

SUMMARY OF THE INVENTION

The disclosed invention comprises a system or kit that includes an undergarment often made from a breathable, absorbent material which has an opening in the crotch area to allow insertive or receptive sex. The undergarment contains at least one pocket that may contain condoms, flavored gels, lubricants, or any other sexual aids, and that may also includes an informational brochure that may discuss safer sex practices or STD information, e.g., symptoms, statistics, and treatment information. The pocket is on the interior side of the undergarment or on the exterior of the undergarment, and may include a cover flap or some means to secure the pocket.

DETAILED DESCRIPTION

Figure 1:
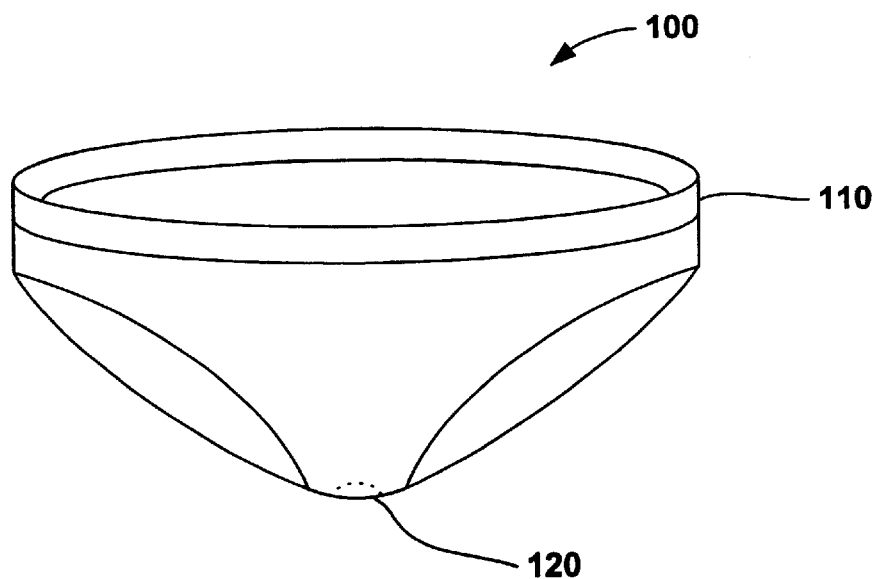
FIG. 1 is a perspective view of the prophylactic undergarment with appropriately placed holes.
Figure 2:
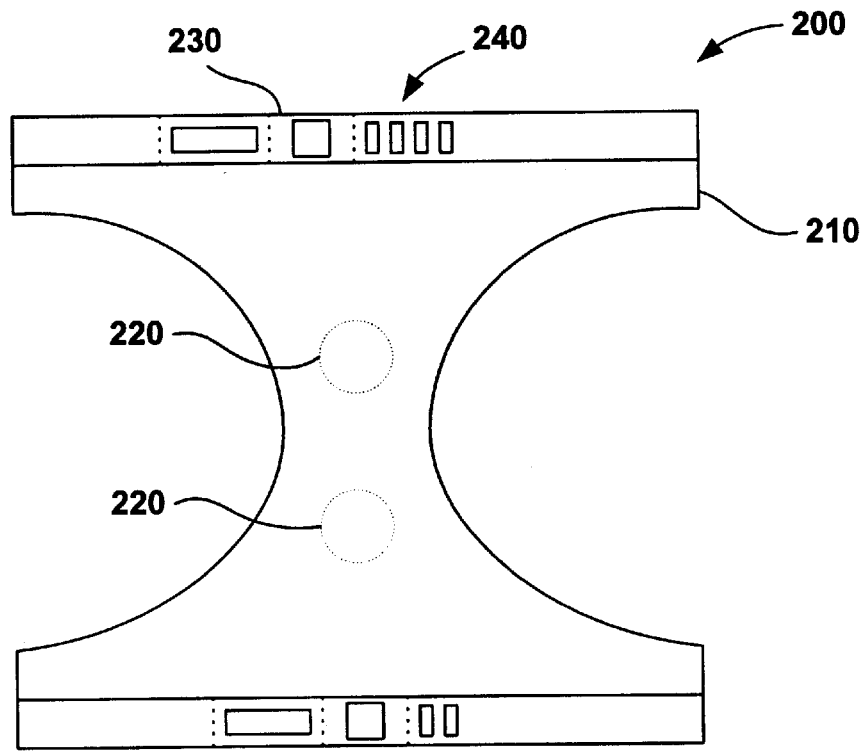
FIG. 2 is a front view of the undergarment with the front and rear panels disconnected to clearly reveal the garment's interior and the system's components.

As shown in FIGS. 1 and 2, the prophylactic system 100, 200 includes undergarment 110, 210 that may be made in the form of men's or women's underwear, depending on the desired wearer. The undergarment 110, 210 is made from a material that can minimize the skin-to-skin contact associated with the sex act, thereby reducing the risk of disease transmission for the wearer. Although the undergarment material is ideally breathable and absorbent such that the material can absorb the fluids associated with the sex act, the material may be of any appropriate material type, e.g., silk, cotton, polyester, Rayon, Spandex, leather, etc. The undergarment 110, 210 includes an appropriately placed hole or series of holes 120, 220 that allow the wearer to continue to wear the undergarment 110, 210 while participating in the desired sexual contact. The undergarment 110, 210 also includes a series of pockets 230 that contain various sexual aids 240. The sexual aids 240 may include, but are not limited to, condoms, lubricants, gels, shower gels, antibacterial cleansers, perfumes, scented oils, lotions, and safer sex information. In variations of the system, the undergarment and associated aids (e.g., the condom and gels) are flavored. Although the flavors associated with the system may be any appropriate flavor for the system's purposes, desirable are flavors such as kiwi, lime, watermelon, peach, pink lemonade, margarita, lemon, smoke, melon, cherry, berry, etc. The flavors associated with the system may also include such commercially available flavors as KiwilimeN'Watermelon, PeachCobbler, Pink Pussycat, Pink Banana Split, HazzleN'Nuts, Rappin Raspberry, Lemon MaraineNCream, Cinnamon Juices, Lucious Liquish, White Chaffon, Red N'Hot, Cherry Berry, Swollowmelon, Popthatcherry, BlackCherry, SassyBerry, BerriesN'Cream, peachesN'me, CreamDreamy, Caramel with Nuts, Banana Nut with Cat, Fruitcocktail, Blast'N'berry, Blowpop, and Sodapop and any combination thereof. Although the undergarment pockets 230 in FIG. 2 are placed on the interior of the undergarment 210, the pockets may also be attached to the exterior of the undergarment 210. Three pockets 230 are displayed in FIG. 2, but the undergarment 210 may contain fewer or more pockets 230. The safer-sex information may include a brochure that details'a number of issues, included but not limited to, safer sex practices, sexually transmitted disease (or STD) statistics, symptoms of STD infection, STD testing information, and information on the proper use of condoms.

Figure 3:
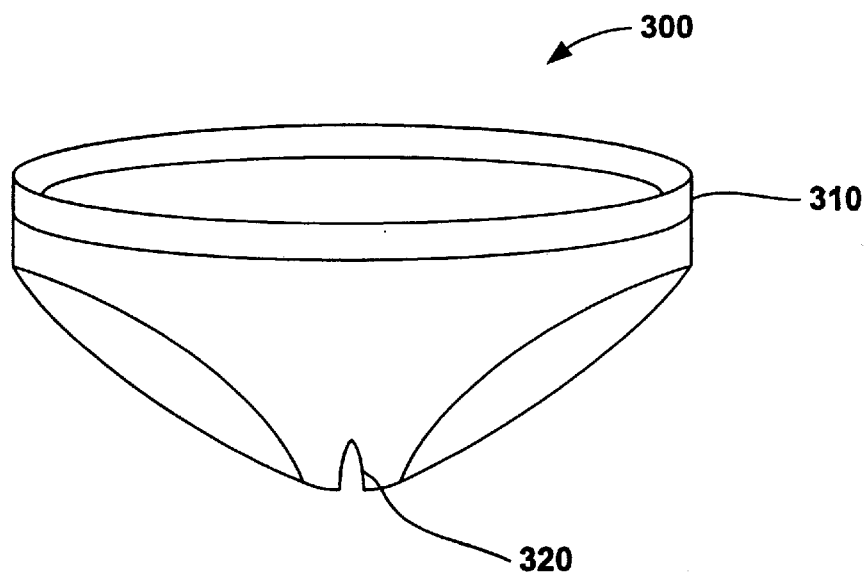
FIG. 3 is a perspective view of a variation of the undergarment with an appropriately placed slit.
Figure 4:
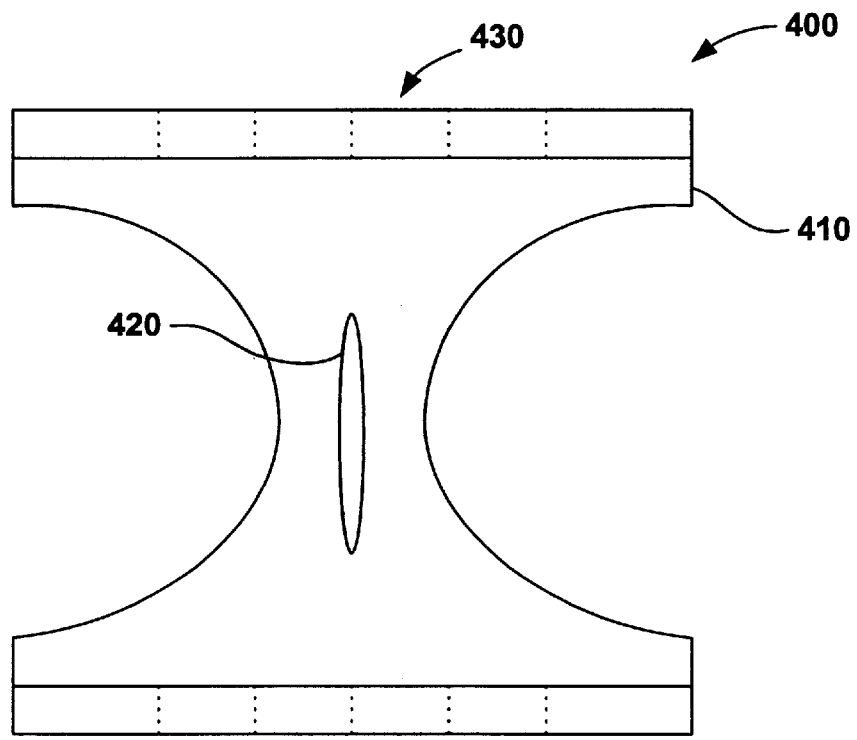
FIG. 4 is a front view of the undergarment with the front and rear panels disconnected to clearly reveal the garment's interior and the system's components.

As shown in FIGS. 1 and 2, the prophylactic system 100, 200 includes an opening to allow sexual contact while the wearer wears the undergarment 110, 210. The means to allow sexual contact may include appropriately placed holes 120, 220, as in FIGS. 1 and 2, a slit, 320 and 420 in FIGS. 3 and 4, which extends throughout the crotch area of the undergarment, or any other means which will allow sexual contact.

Figure 5:
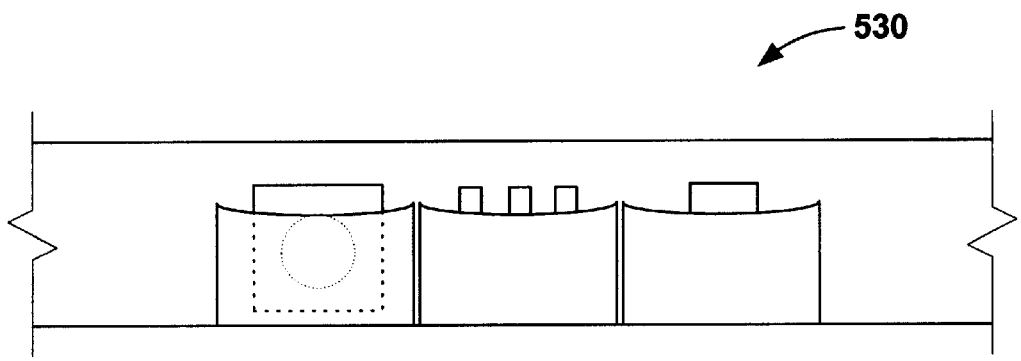
FIG. 5 is a sectional view of the prophylactic undergarment detailing the pockets which contain the system's condom, lubricant, flavored gels, and safer sex informational brochure.
Figure 6:
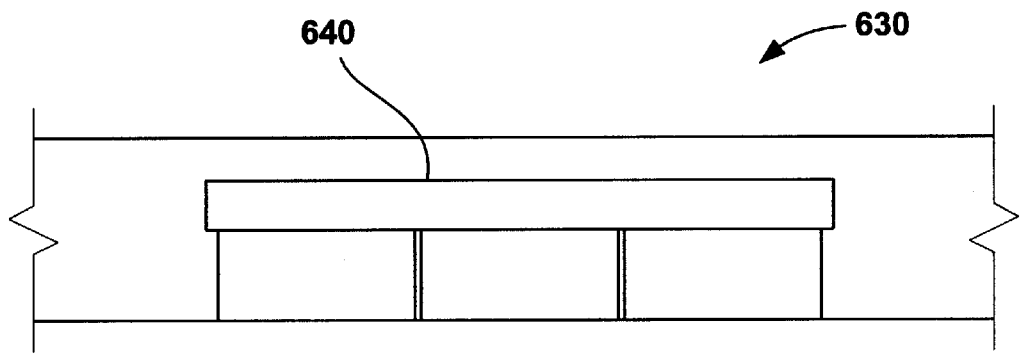
FIG. 6 is a sectional view of the prophylactic undergarment detailing a variation of the pocket.

As FIG. 5 displays, the pocket(s) 530 associated with the system may be an integral part of the undergarment or attached later to the undergarment via an appropriate attachment means, e.g., the pockets may be sewn or glued to the undergarment or may contain a hook and loop material such as Velcro such that they can be removably attached to the undergarment. A variation of the pockets detailed in FIG. 6 has an associated closing-flap 640. The pockets 530, 630 may be located on the interior or exterior of the undergarment.

Figure 7:
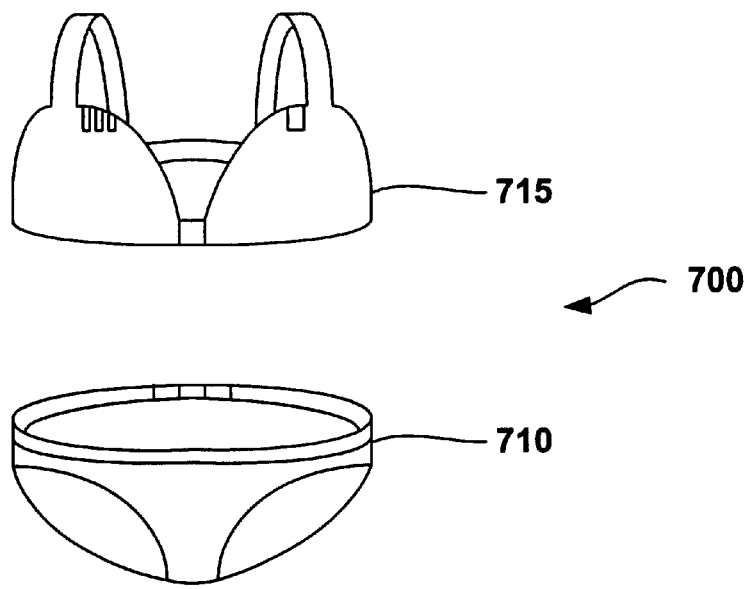
FIG. 7 is a perspective view of a variation of the prophylactic undergarment that displays a brassiere and matching panties which both contain pockets with sexual aids and a safer-sex brochure.

The undergarment may take the form of women's panties, brassieres, briefs, boxers, any other form of undergarment or any combination thereof. FIG. 7 displays a prophylactic system 700 for which the undergarment is in the form of a women's panty 710 and bra 715.

Figure 8:
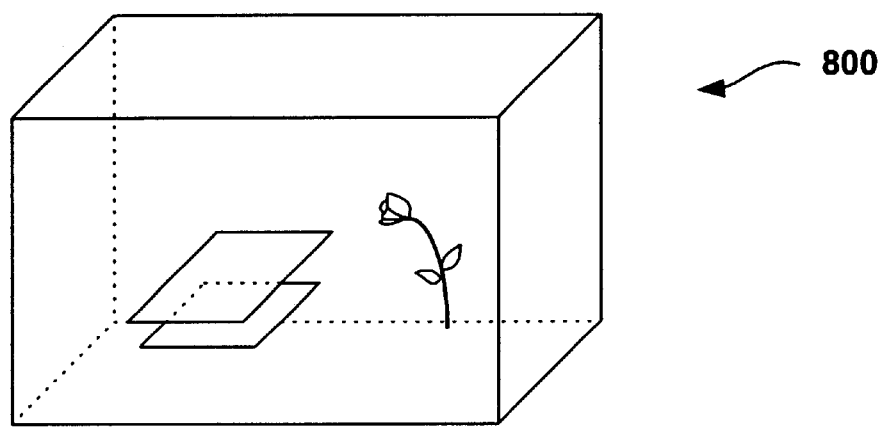

As FIG. 8 displays, the system may include some form of packaging 800 that allows easier marketing. The packaging may include but is not limited to a toy, a balloon, a music box, a stuffed animal, a jewelry box, etc. and the packaging may include other items, e.g., as flowers, toys, candy, jewelry, stuffed animals, at-home STD testing kits, etc. The toys may be any item that can be associated with the system and may include toy boats, toy cars, or a toy animal (e.g., fish).

Many alterations and modifications may be made by those of ordinary skills in the art without departing from the spirit and scope of this invention. The illustrated embodiments have shown only for purposes of clarity. The examples should not be taken as limiting this invention as defined by the following claims; the invention claims all equivalents, whether those equivalents are now or later devised.

What is claimed is:

1. A prophylactic system for use by human wearer comprising:

an undergarment having an opening which is appropriately placed to allow for sexual contact while the undergarment is worn;

at least one pocket secured to the undergarment;

a condom contained within the at least one pocket;

a packet of sexual aids contained within the at least one pocket; and an informational brochure contained within the at least one pocket.

2. The system of claim 1 wherein the undergarment is made of an absorbent material such that fluids associated with intercourse are absorbed by the undergarment.

3. The system of claim 1 wherein any of the undergarment, condom and sexual aids is flavored.

4. The system of claim 1 wherein the condom is color coordinated with the undergarment.

5. The system of claim 1 wherein the undergarment comprises a panty and matching brassiere.

6. The system of claim 1 wherein the packet of sexual aids contains sexual aids selected from the group consisting of lubricants, flavored gels, shower gels, antibacterial cleansers, perfumes, and lotions.

7. The system of claim 1 wherein the informational brochure details information selected from the group consisting of safe sex procedures, the proper use of condoms, the proper use of the sexual aids included in the system, and STD information.

8. The system of claim 1 further comprising packaging enclosing said undergarment, condom, pocket, and informational brochure.

9. The system of claim 3 where the flavors are selected from the group consisting of kiwi, lime, watermelon, peach, pink lemonade, margarita, lemon, smoke, melon, cherry, berry, KiwilimeN'Watermelon, PeachCobbler, Pink Pussycat, Pink Banana Split, HazzleN'Nuts, Rappin Raspberry, Lemon MaraineNCrearn, Cinnamon Juices, Lucious Liquish, White Chaffon, Red N'Hot, Cherry Berry, Swollowmelon, Popthatcherry, BlackCherry, SassyBerry, BerriesN'Cream, peachesN'me, CreamDreamy, Caramel With Nuts, Banana Nut with cat, Fruitcocktail, Blast'N'berry, Blowpop, and Sodapop.

* * * * *